United States Patent [19]

Bell et al.

[11] Patent Number: 4,978,689

[45] Date of Patent: Dec. 18, 1990

[54] CONVERSION OF SYNTHESIS GAS TO LIQUID HYDROCARBONS

[75] Inventors: Weldon K. Bell, Pennington; Werner O. Haag, Lawrenceville, both of N.J.

[73] Assignee: Mobil Oil Corp., Fairfax, Va.

[21] Appl. No.: 324,795

[22] Filed: Mar. 17, 1989

[51] Int. Cl.$^5$ .................................................. C07C 1/04
[52] U.S. Cl. .................................... 518/709; 518/700; 518/713
[58] Field of Search ...................... 518/709, 711, 700

[56] References Cited

U.S. PATENT DOCUMENTS

| | | | |
|---|---|---|---|
| 2,497,964 | 2/1950 | Sumerford | 518/711 |
| 2,544,574 | 3/1951 | Walker et al. | 518/709 |
| 4,252,736 | 2/1981 | Haag et al. | 260/450 |
| 4,338,089 | 7/1982 | Schaper et al. | 518/707 |

FOREIGN PATENT DOCUMENTS

| | | | |
|---|---|---|---|
| 518486 | 11/1955 | Canada | 518/711 |
| 535631 | 1/1957 | Canada | 518/711 |

OTHER PUBLICATIONS

L. Koenig et al., "The Influence of Water and of Alkali Promoter on the Carbon Number Distribution, etc." Ber. Bunsenges. Phys. Chem., 91, 116–121 (1987).

*Primary Examiner*—Howard T. Mars
*Attorney, Agent, or Firm*—Alexander J. McKillop; Charles J. Speciale; Dennis P. Santini

[57] ABSTRACT

The medium pressure Fischer-Tropsch synthesis of liquid hydrocarbons conducted with an iron catalyst is made more efficient by temporarily suspending conventional synthesis and treating the catalyst with a high partial pressure of water vapor, after which conventional synthesis is resumed. The treatment inparts a large increase in selectivity for liquids with reduction of methane formation. The treatment is very effective with alkali (e.g. potassium) promoted precipitated iron catalyst.

6 Claims, 5 Drawing Sheets

CONVERSION OF SYNTHESIS GAS TO LIQUID HYDROCARBONS

FIELD OF THE INVENTION

This invention is concerned with the conversion of synthesis gas, i.e. mixtures of gaseous carbon oxide with hydrogen or hydrogen donors, to hydrocarbon mixtures. In particular, it is concerned with improving the efficiency of the process by interrupting normal synthesis to "selectivate" (i.e. improve selectivity) of the catalyst.

BACKGROUND OF THE INVENTION

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. An excellent summary of the art of gas manufacture is given in Encyclopedia of Chemical Technology, Edited by Kirk-Othmer, Second Edition, Volume 10, pages 353–433, (1966), Interscience Publishers, New York, N. Y., the contents of which are herein incorporated by reference. The techniques for gasification of coal or other solid, liquid or gaseous fuel are not per se considered part of the present invention.

It is known that synthesis gas can be converted to reduction products of carbon monoxide, such as hydrocarbons, at from about 150° C. to about 450° C., under from about- one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides. The wide range of catalysts and catalyst modifications disclosed in the art and an equally wide range of conversion conditions for the reduction of carbon monoxide by hydrogen provide some flexibility toward obtaining selected types of products, and some control over their molecular weight distribution Ruthenium catalyst, for example, is capable of producing linear hydrocarbons exclusively, while "promoted iron" also produces oxygenates. Nonetheless, these conversions still leave much to be desired because either the catalyst is costly or by-products are produced in excessive amount. A review of the status of this art is given in "Carbon Monoxide-Hydrogen Reactions", Encyclopedia of Chemical Technology, Edited by Kirk-Othmer, Second Edition, Volume 4 pp. 446–488, Interscience Publishers, New York, N. Y., the text of which is incorporated herein by reference for background.

The molecular weight distribution of the product in the Fischer Tropsch reaction is controlled to a great extent by the nature of the reaction, and it is generally recognized that the steady state products of the reaction follow the Schulz-Flory distribution. See, e.g., P. Biloen and W.M.H. Sachtler, *Advance-in Catalysis*, Vol. 30, pp. 169–171 (Academic Press, New York, N. Y., 1981), which is herein incorporated by reference for background. Very briefly, for this is well described elsewhere, if the synthesis that takes place is characterized by a stepwise addition of a single carbon species to a growing hydrocarbon chain with a propagation rate constant $k_p$, and if this step competes with a growth-terminating step having the rate constant $k_t$, then the chances for any intermediate species to propagate rather than terminate is described by , wherein $$\alpha = k_p/(k_p+k_t)$$

If $\alpha$ is independent of the molecular weight of the intermediate, $$\log C_n = \text{Constant} + n(\log \alpha)$$

where $C_n$ is the mole percent of the (n)th-mer in the product and n is the number of carbon atoms contained in that species. A plot of $\log C_n$ vs n provides a straight line with the slope $\log \alpha$.

The significance of the foregoing relationship for producing hydrocarbons by the Fischer Tropsch process is that a reduction of by-product methane formation also reduces larger amounts of $C_2$, $C_3$, and $C_4$ hydrocarbons and causes a significant increase in the total yield of $C_5$+liquids, with more liquid in the diesel fuel range being formed.

In brief, when practitioners in the Fischer Tropsch art refer to the selectivity of a catalyst or process in terms of the relative amount of methane that is produced, it is generally understood in the context of the overall changes in the distribution of normally gaseous and liquid hydrocarbon product as outlined above. It is generally recognized in this art, however, that selectivity is a function not only of the catalyst composition and its method of preparation, but also is a function of process conditions, particularly temperature, and a function of synthesis gas composition. In general, a *decrease* in temperature results in improved selectivity for liquid hydrocarbons, and a similar result tends to be achieved with a synthesis gas that, within limits, is relatively rich in carbon monoxide. In principle, of course, selectivity for increased liquid hydrocarbons can be obtained by simply lowering temperature, but such an expedient also lowers conversion. As a practical matter, there is a lower temperature limit, dictated by the economically required conversion rate, below which operation becomes impractical.

Precipitated iron catalysts have been extensively studied and have been used for many years in the Fischer-Tropsch liquid phase process for synthesis of hydrocarbons. In general, they are inexpensive, exhibit good activity, and have adequate useful life. They almost always contain potassium promoter, which serves to reduce the amount of methane and other light hydrocarbon by-products. However, the amount of potassium that is normally used is limited to about 0.6 wt%, since larger amounts do not appear to offer further benefit with regard to methane reduction, and in fact increase the production of oxygenated by-products. Thus, there is a need for an iron catalyst having a higher selectivity for liquid hydrocarbons than is presently achieved in order to increase the total liquid hydrocarbons formed, especially those in the boiling range of high quality diesel fuel.

Conventional techniques for the production of a precipitated, inactive iron catalyst in large quantity and its activation prior to use are described by H. Koebel and M. Ralek, Catalysis Review-Sci Eng (1980) *Volume 21*, pp. 242-249, the entire content of which is incorporated herein by reference as if fully set forth. The initial steps in the preparation of the precipitated inactive iron catalyst useful in this invention are conventional. Ferric nitrate, which may be obtained by dissolving wrought iron scrap or steel turnings in nitric acid or, alternatively, from another source, is dissolved in water. The solution should be adjusted, if necessary, so that it contains a predetermined small amount of copper. The iron is then precipitated with ammonia or ammonium carbonate. Potassium carbonate is then added to the filtered and washed precipitate to provide a content of 0.1 to about 1.0 wt% potassium carbonate based on iron. The preferred potassium carbonate level is about 0.2 to 0.6 wt% based on iron content.

The filter cake produced by the technique just described and followed by the conventional step of calcining in air at e.g. 572° F, usually contains well in excess of 1000 ppm (parts per million) of nitrogen. For certain special applications, an iron catalyst having a nitrogen content less than 200 ppm, preferably less than 100 ppm, may be needed. Such catalyst may be prepared by bringing together the ammonia solution and the ferric nitrate solution at controlled rates such that the pH of the cooled supernatant liquid containing the precipitated catalyst is maintained at about 6.8. The filter cake produced by this method is then washed with hot water until relatively free of nitrate ion. The resulting calcined filter cake produced by this technique is of low nitrogen content For further details, see U.S. 4,617,288 to Bell et al., incorporated herein by reference.

It is generally known that iron catalysts, as initially formed, are inactive in the Fischer Tropsch synthesis. Before use in the synthesis process, they must be subjected to an activation step which comprises contacting the inactive solid with a reducing gas, such as synthesis gas, at elevated temperature.

During activation, the iron is partially reduced to the metallic bonding state. This activation is conducted in the absence of water.

Water is known to be a powerful inhibitor in the Fischer Tropsch synthesis. Carbon dioxide is also an inhibitor, but very much weaker than water. The primary step in the conversion produces water by reaction (I): $2H_2 + CO \rightarrow -CH_2- + H_2O$, (I) but much of the water is consumed by the shift reaction (II) catalyzed by the iron catalyst:

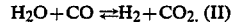

$$H_2O + CO \rightleftharpoons H_2 + CO_2 \text{ (II)}$$

To minimize the inhibiting effect of water, the synthesis gas feed to the Fischer Tropsch process and the recycle streams usually are dried prior to contact with the iron catalyst.

It is known that the catalyst life of an iron catalyst used in the Fischer-Tropsch process is limited by loss of activity during synthesis. For example, catalyst life of six months was reported for a fixed-bed unit that employed an alkaline, precipitated iron catalyst. During the six-month period, the operating temperature was increased from the starting point of 220° C to a maximum of 255° C. This temperature compensation for loss of activity certainly incurs a substantial loss of selectivity.

Koenig et al., in Ber. Bunsenges. Phys. Chem. 91, 116-21 (1987), report the results of an investigation of the influence of water and of alkali promoter on carbon number distribution of products formed over iron catalyst. U.S. 4,252,736 to Haag et al. discloses and claims adding water or steam to the Fischer-Tropsch conversion zone to adjust the H2/CO ratio of a syngas feed containing excessive hydrogen. Neither of these references disclose the present invention.

It is an object of this invention to provide a method for improving the selectivity of a used Fischer-Tropsch iron catalyst. It is a further object of this invention to provide a method for restoring the selectivity of a Fischer-Tropsch precipitated iron catalyst which has decayed during use. These and other objects will become apparent to one skilled in the art on reading this entire specification including appended claims.

SUMMARY OF THE INVENTION

We have now found that the selectivity of an iron catalyst that is in use in the Fischer-Tropsch synthesis of hydrocarbons is improved by the following steps:

(1) suspending said synthesis;

(2) treating the catalyst for about 1 (one) to about 10 hours with water vapor under a combination of conditions including a temperature of 160° to 400° C, a total pressure of 10 to 1000 psig, and a partial pressure of water vapor effective to selectivate said catalyst; and, (3) resuming the synthesis with a substantially dry mixture of carbon monoxide and hydrogen, whereby increasing the efficiency of said process for synthesizing liquid hydrocarbons, all as more fully described hereinbelow.

The principal effect of the treatment is improvement of the *selectivity* of the used catalyst with no substantial change of activity. We shall herein refer to this treatment as "selectivation".

DETAILED DESCRIPTION, PREFERRED EMBODIMENTS AND BEST MODE

Figure 1A:
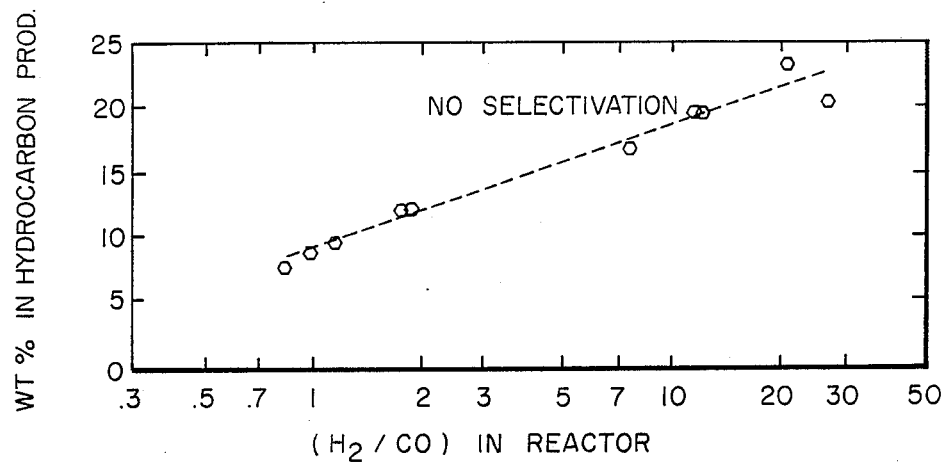
FIGS. 1A and 1B respectively show methane and liquid hydrocarbon ($C_5+$) selectivity as a function of feed composition for Example 1B.

The particular Fischer-Tropsch conversion process that benefits from use of the present invention is commonly characterized as a "medium pressure" synthesis, and utilizes an iron catalyst. Medium pressure synthesis (with iron catalyst) is conducted at approximately 150 to 450 psig total pressure. Catalyst life is favored by operating at high space velocities. Fixed (static) bed, entrained fluid-bed and slurry reactors may be used, although other variants such as fixed fluid-bed and oil-submerged catalyst have been studied. The fixed-bed and entrained fluid-bed are of commercial importance. The fixed-bed version utilizes precipitated iron catalyst promoted with potassium and copper, and the entrained fluid-bed version a fused magnetite promoted with potassium and other optional promoters including structural promoters such as MgO. Operating temperatures fall into the approximate range of 220° to 350° C, with the fixed-bed process operation being in the range of about 220°–255° C. In the fixed-bed process, a catalyst life of six to twelve months is achieved during which the operating temperature is increased from the starting point of 220° C to a maximum of 255° C. For further details on the commercial process, see "Carbon Monoxide - Hydrogen Reactions", Ibid, esp. pp. 465-477 and references contained therein. The foregoing description refers to the conventional versions of the Fischer-Tropsch process for synthesizing hydrocarbons with iron catalyst, and is not per se considered part of the present invention.

The conventional synthesis described above is improved in efficiency by temporarily suspending the conventional synthesis to "selectivate" the catalyst with water vapor, as more fully described below. Following selectivation, normal synthesis is resumed. Maintaining the same operating conditions as before selectivation results in improved yield of liquid hydrocarbons with increased yields of oil boiling in the diesel fuel range and decreased yields of methane, C2 and C3 hydrocarbons. Additionally, with precipitated iron catalyst, the run may be conducted to higher than conventional 255° C end-of-run temperatures without encountering uneconomical levels of methane formation. Other process optimizations are permitted by the improved process of this invention, including increasing operating temperature on resumption of synthesis to increase conversion rate without a selectivity penalty, as indicated above.

The preferred variant of the Fischer-Tropsch process for purposes of this invention is that which uses a precipitated iron catalyst that contains potassium promoter in the range equivalent to 0.2 to 0.6 wt% potassium carbonate. Although potassium is the preferred alkali promoter, it is contemplated that other alkali metals also would be operative in this invention.

The necessary "selectivation" step in the improved process of this invention requires that the iron catalyst be exposed at elevated temperature to a sufficiently high water vapor pressure to induce substantial selectivation, i.e. a reduction of at least about 1 wt% of methane in total hydrocarbon product, when steadystate synthesis is resumed at the same conditions that prevailed before suspension of conventional synthesis. An insufficient water vapor pressure, e.g. that which exists during conventional synthesis, is not effective to induce selectivation even after many hours or days on stream. However, the precise value of water vapor pressure at which selectivation occurs depends on temperature, time, and whether or not reducing gases are present.

Selectivation may be conducted with substantially pure steam, such as is provided by a conventional steam boiler, or with such steam diluted with an inert gas such as nitrogen, carbon dioxide, or a mixture thereof. Use of inert diluent is preferred to allow better control of water vapor partial pressure. The selectivation step may be conducted by transferring the catalyst from the Fischer-Tropsch reactor to a separate vessel in which the selectivation treatment is conducted. However, it is much simpler to avoid the transfer, and therefore it is preferred to conduct the treatment in situ, a matter easily arranged by providing the necessary piping and valves. In situ selectivation is preferably conducted with a flowing stream of water vapor, as further described below.

The conditions contemplated as effective for the use of pure steam, with and without optional $N_2$ and/or $CO_2$ diluent, are given in Table A.

TABLE A

| | Selectivation with Flowing $H_2O$ Vapor and Optional Inert Gas (G). | | | |
|---|---|---|---|---|
| | Temperature, °C. | Pressure psig | Time hrs. | $H_2O^*$ $H_2O + G$ |
| Broad | 160–400 | 10–1000 | 0.5–100 | 0.05–1.0 |
| Preferred | 190–350 | 15–500 | 1–35 | 0.1–1.0 |
| Partic. Pref'd. | 210–290 | 30–250 | 2–20 | 0.3–1.0 |

*Mole Ratio of Water in Feed.

Selectivation also may be conducted with steam utilizing synthesis gas or hydrogen gas as diluent, as illustrated later by example. In this instance we have found that CO increases the required partial pressure of water vapor for substantial selectivation. Conditions contemplated as useful for effective selectivation with such diluents are given in Table B.

TABLE B

| | Selectivation with Flowing $H_2O$ Vapor and Co-Fed Syngas or Hydrogen | | | | |
|---|---|---|---|---|---|
| | Temperature, °C. | Pressure psig | Time, hrs. | $H_2O^*$ $H_2 + CO + H_2O$ | $H_2^*$ $H_2 + CO$ |
| Broad | 160–400 | 100–1000 | 0.5–100 | 0.2–1.0 | 0–1.0 |
| Preferred | 190–350 | 150–500 | 1–35 | 0.25–0.75 | 0.2–0.9 |
| Partic. Pref'd. | 210–290 | 180–250 | 2–20 | 0.3–0.6 | 0.33–0.75 |

*Mole Ratios in Feed.

The improved process of this invention may be employed in different situations. A catalyst that has been imperfectly activated and put on stream may be found after a very short time, such as 24 to 48 hours, to show poor activity. It is contemplated to improve such catalyst by the procedure of this invention. A catalyst that has undergone substantial aging after several months on stream can be treated as described herein to impart improved selectivity. And, a selectivated, virgin catalyst prepared according to copending U.S. Patent Application, Serial No. 07/324,796, filed on even date herewith, after use for a sufficient time to undergo loss of selectivity may be treated as described herein. The foregoing are non-limiting examples of a catalyst "used in the Fischer-Tropsch process" that are contemplated as benefiting from the method of this invention.

EXAMPLES

This invention will now be illustrated by example. The examples, however, are not to be construed as limiting the scope of the invention, which scope is determined by this entire specification including appended claims All selectivities given herein are by weight percent; all catalyst composition are by weight; all ratios are molar ratios; and all syngas conversions are mole percent unless explicitly stated to be otherwise.

In the examples which follow, all of the selectivity values and other kinetic data were obtained by charging finely ground (inactive) iron catalyst (providing about 5 grams of Fe) to a continuous stirred tank reactor (CSTR) of 300 ml capacity that contained 120 to 200 cc hydrogenated decene trimer in which the catalyst is suspended (slurry reactor). The catalyst was then activated and selectivated as described in the specific examples.

After activation, catalyst behavior was determined by isothermal synthesis mostly conducted at about 265° C, with specific exceptions as may be shown in the Tables, and at about 235 psi and with high (1.9) and low (0.6) $H_2/CO$ ratio syngas feeds at various feed rates. With the CSTR system, it was possible, using these feeds, to vary the $H_2/CO$ ratio in the reactor and reactor effluent over a wide range (from 0.6 to 30) by the simple expedient of varying the syngas feed rate.

Figure 2A:
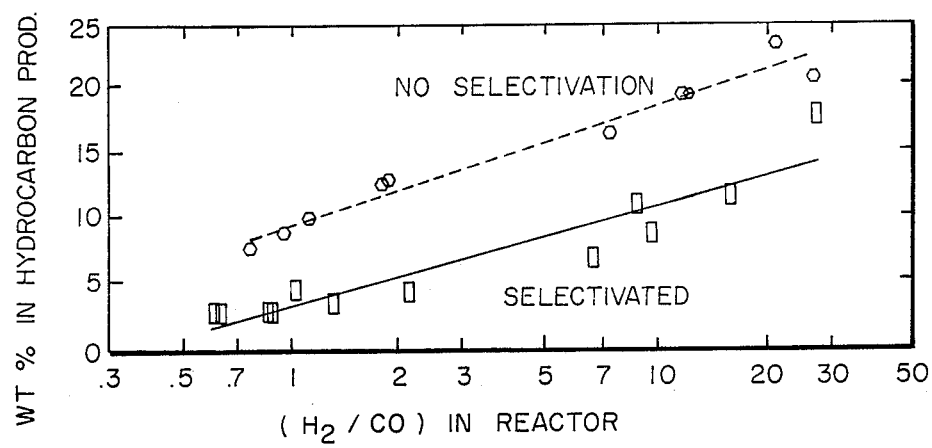
FIGS. 2A and 2B respectively show methane and liquid hydrocarbon ($C_5+$) selectivity as a function of feed composition for Example 2.
Figure 2B:
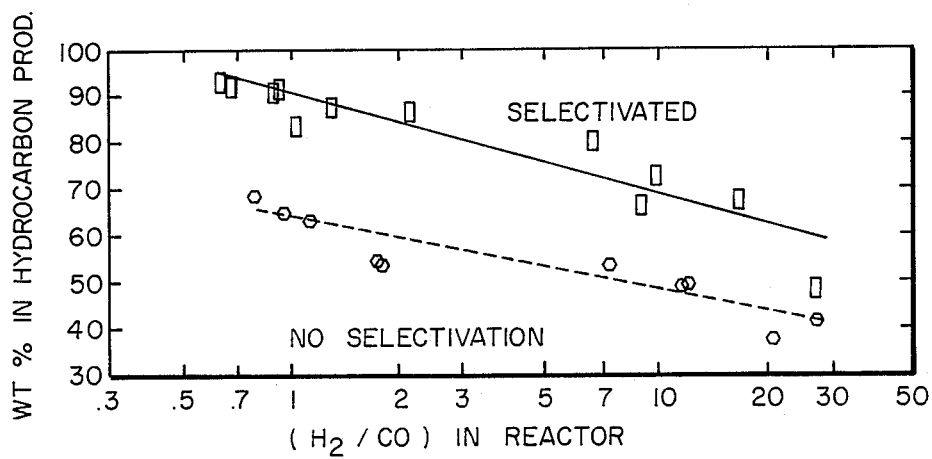

FT catalyst selectivity was assessed by correlation with $H_2/CO$ ratio during reaction. This ratio is directly measured as that exiting from the CSTR. Selectivity was correlated with the $H_2/CO$ ratio as shown in FIGS. 2A and 2B. This technique allows selectivity comparisons that are independent of conversion. The left portion of the illustration is behavior typical of low $H_2/CO$ feeds as from advanced coal gasifiers, while the right portion is typical of $H_2$-rich feeds as from methane reformers.

EXAMPLE 1A

This example illustrates the preparation of a precipitated iron catalyst. Example 1B which follows illustrates conventional activation. Neither Example 1A nor 1B are considered part of the present invention, and are given only to provide selectivity and other data for comparison purposes.

Catalyst preparation was as follows. A stirred flask warmed with a heating mantle and equipped with a reflux condenser to minimize $NH_3$ loss. A 1360 gram portion of a 10 wt% $NH_3$ solution was quickly poured into a hot (102° C) 1640-ml aqueous solution of 808 grams $Fe(NO_3)_3 \cdot OH_2O$ and 1.28 grams $Cu(NO_3)_2 \cdot 3.1 H_2O$ with stirring rapid precipitation resulted. The mixture pH varied from 6.9 just after base addition to 6.5 after the slurry temperature had returned to about 96° C (approximately 5 minutes), digesting continued for another 18 minutes. The slurry was filtered in two equal portions Each filter cake was washed with about 3.5 liters of hot (90° -100° C.) water in 17 ½ 200 ml portions. A 30 gram portion of the filter cake was reserved leaving a 1048 gram portion containing an estimated 107 gram Fe. This large portion was slurried with an added 1.4 liters water and then a 1025 ml of solution containing 0.615 gram $K_2CO_3$ was slowly added. The slurry was then filtered (but not washed), dried overnight in the filter at room conditions, dried in air at 120° C. for 17 hours, and calcined at 320° C. for 6 hours. Assay indicated that $Fe/Cu/K_2CO_3$ was 100/0.2/0.4 parts by weight.

EXAMPLE 1B

In this example a portion of the inactive iron catalyst prepared in Example 1A was ground, charged to the slurry CSTR reactor described above, and activated in conventional manner by passing through the reactor 6 NL/FGe/HR (Normal liters, i.e. liters of $H_2/CO$, at 273° K and 1 atmosphere per gram of iron per hour) of dry syngas having a $H_2/CO$ ratio of about 0.7 for 3 to 5 hours at a pressure of 35 psi, while maintaining the reactor temperature at 280° -290° C.

After activation, the temperature was dropped and maintained at about 265° -266° C. and the pressure increased while continuing to feed syngas. The data obtained for different syngas compositions and at different space velocities are summarized in Table I.

Figure 1B:
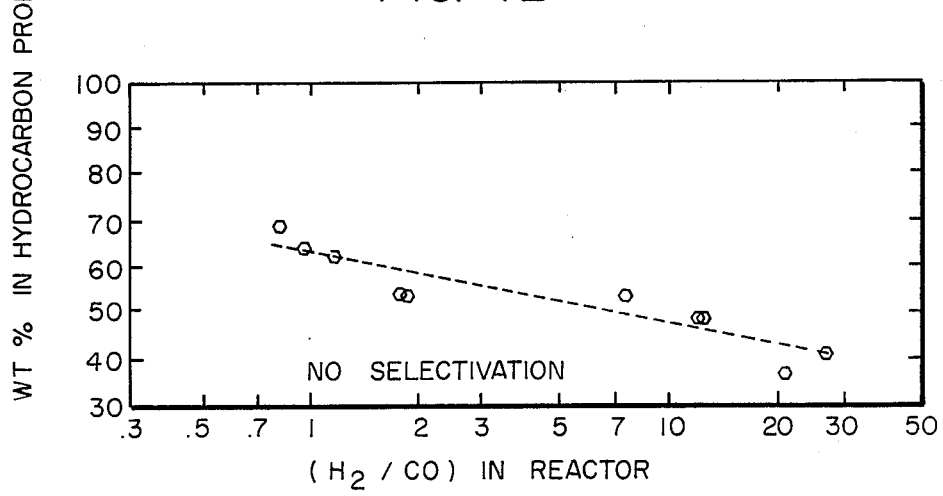

The methane selectivity of the catalyst and the selectivity for liquid hydrocarbons as a function of feed composition are shown in FIGS. 1A and 1B, respectively.

TABLE I
(EXAMPLE 1B)
PRIOR ART CATALYST PERFORMANCE

| RUN BALANCE | A | B | C | D | E |
|---|---|---|---|---|---|
| HOURS ON STREAM | 19.25 | 21.00 | 24.68 | 43.52 | 46.50 |
| TEMPERATURE °C. | 266.00 | 266.00 | 266.00 | 266.00 | 266.00 |
| PRESSURE PSIG | 202.00 | 202.00 | 202.00 | 202.00 | 202.00 |
| SV NL/GFE/HR | 1.27 | 3.54 | 2.52 | 0.64 | 3.70 |
| FEED [$H_2$/CO] | 0.72 | 0.72 | 0.72 | 0.72 | 0.72 |
| SYNGAS CONV % | 90.44 | 72.87 | 81.29 | 91.92 | 59.69 |
| $H_2$ CONV % | 85.36 | 68.23 | 75.97 | 87.42 | 56.90 |
| CO CONV % | 94.10 | 76.22 | 85.12 | 95.17 | 61.71 |
| HYDROCARBON SELECTIVITIES, WT % OF HC | | | | | |
| CH4 | 12.26 | 9.00 | 9.76 | 12.42 | 7.74 |
| $C_2H_6$ | 8.74 | 5.74 | 6.42 | 8.92 | 3.59 |
| $C_2H_4$ | 0.69 | 1.96 | 1.32 | 0.63 | 2.73 |
| $C_3H_8$ | 7.48 | 3.00 | 3.59 | 8.29 | 1.69 |
| $C_3H_6$ | 6.91 | 8.90 | 8.53 | 6.66 | 8.28 |
| $C_4H_{10}$ | 3.86 | 2.22 | 2.43 | 3.90 | 1.60 |
| $C_4H_8$ | 5.81 | 5.78 | 5.65 | 5.85 | 5.59 |
| $C_5+$ | 54.25 | 63.41 | 62.31 | 53.32 | 68.80 |
| EXIT [$H_2$/CO] | 1.79 | 0.96 | 1.16 | 1.88 | 0.81 |
| [$H_2 + CO_2/H_2O + CO$] | 39.00 | 11.73 | 20.64 | 56.16 | 9.59 |

| RUN BALANCE | F | G | H | T | J |
|---|---|---|---|---|---|
| HOURS ON STREAM | 66.72 | 70.83 | 72.67 | 91.53 | 95.33 |
| TEMPERATURE °C. | 265.00 | 265.00 | 265.00 | 265.00 | 265.00 |
| PRESSURE PSIG | 202.00 | 202.00 | 202.00 | 202.00 | 202.00 |
| SV NL/GFE/HR | 0.61 | 3.64 | 2.48 | 0.31 | 1.26 |
| FEED [$H_2$/CO] | 1.87 | 1.87 | 1.87 | 1.87 | 1.87 |
| SYNGAS CONV % | 64.12 | 51.52 | 56.81 | 68.87 | 57.54 |
| $H_2$ CONV % | 47.52 | 34.52 | 38.97 | 53.99 | 39.87 |

TABLE I-continued
(EXAMPLE 1B)
PRIOR ART CATALYST PERFORMANCE

| | | | | | |
|---|---|---|---|---|---|
| CO CONV % | 95.21 | 83.35 | 90.24 | 96.73 | 90.65 |
| HYDROCARBON SELECTIVITIES, WT % OF HC | | | | | |
| $CH_4$ | 23.07 | 16.45 | 19.21 | 20.14 | 19.32 |
| $C_2H_6$ | 10.74 | 6.05 | 7.58 | 10.14 | 7.61 |
| $C_2H_4$ | 1.25 | 1.74 | 1.38 | 1.50 | 1.29 |
| $C_3H_8$ | 7.44 | 3.77 | 4.86 | 6.51 | 4.75 |
| $C_3H_6$ | 9.33 | 9.10 | 9.17 | 10.37 | 9.19 |
| $C_4H_{10}$ | 4.39 | 3.30 | 3.64 | 4.07 | 3.69 |
| $C_4H_8$ | 5.87 | 6.21 | 6.08 | 6.38 | 6.01 |
| $C_5+$ | 37.91 | 53.37 | 48.09 | 40.88 | 48.15 |
| EXIT [$H_2/CO$] | 20.52 | 7.36 | 11.72 | 26.32 | 12.04 |
| [$H_2 + CO_2/H_2O + CO$] | 48.53 | 30.72 | 34.96 | 44.59 | 42.89 |

EXAMPLE 2

In this example a portion of the inactive iron catalyst from Example 1A was activated in the conventional manner in the backmixed reactor by the procedure described in Example 1B. After activation, the catalyst was selectivated by contact at 261° C for 32 hours with a stream of $N_2$ gas and water vapor at about 12 atmospheres total pressure. The water was fed at 0.44 $g/g_{Fe}/hr$, providing a partial pressure of 5 atmospheres of steam in the reactor.

Following activation, the temperature was maintained at 265°–266° C. while syngas was fed as in Example 1B. The data obtained for different syngas compositions and at different space velocities are summarized in Table II. FIGS. 2A and 2B illustrate the marked increase in selectivity compared with Example 1B over a wide range of conditions. As is evident from Table II, no loss of activity results from selectivation.

TABLE II
(EXAMPLE 2)

| RUN BALANCE | A | B | C | D | E | F |
|---|---|---|---|---|---|---|
| HOURS ON STREAM | 94.83 | 99.92 | 118.75 | 125.58 | 142.83 | 148.33 |
| TEMPERATURE °C. | 266.00 | 265.00 | 266.00 | 265.00 | 266.00 | 266.00 |
| PRESSURE PSIG | 230.00 | 230.00 | 230.00 | 230.00 | 230.00 | 230.00 |
| SV NL/GFE/HR | 1.25 | 2.40 | 0.68 | 2.45 | 0.31 | 1.25 |
| FEED [$H_2/CO$] | 0.63 | 0.63 | 0.63 | 1.92 | 1.92 | 1.92 |
| SYNGAS CONV % | 68.73 | 67.35 | 86.76 | 55.49 | 64.18 | 51.48 |
| $H_2$ CONV % | 61.24 | 60.27 | 80.38 | 39.08 | 47.47 | 33.07 |
| CO CONV % | 73.46 | 71.81 | 90.78 | 87.05 | 96.31 | 86.91 |
| HYDROCARBON SELECTIVITIES, WT % OF HC | | | | | | |
| $CH_4$ | 2.34 | 2.43 | 3.35 | 10.97 | 17.52 | 9.02 |
| $C_2H_6$ | 0.55 | 0.50 | 1.17 | 4.35 | 8.33 | 2.52 |
| $C_2H_4$ | 1.55 | 1.63 | 1.79 | 2.64 | 2.79 | 2.84 |
| $C_3H_8$ | 0.37 | 0.43 | 0.64 | 2.25 | 4.37 | 1.86 |
| $C_3H_6$ | 2.38 | 2.46 | 3.41 | 7.17 | 9.58 | 4.85 |
| $C_4H_{10}$ | 0.36 | 0.42 | 0.58 | 1.94 | 2.94 | 1.63 |
| $C_4H_8$ | 1.84 | 1.92 | 2.74 | 5.33 | 5.44 | 3.86 |
| $C_5+$ | 90.62 | 90.21 | 86.32 | 65.34 | 49.01 | 73.41 |
| EXIT [$H_2/CO$] | 0.92 | 0.89 | 1.34 | 9.05 | 27.39 | 9.84 |
| [$H_2 + CO_2/H_2O + CO$] | 16.96 | 18.11 | 38.81 | 34.12 | 56.92 | 36.77 |

| RUN BALANCE | G | H | I | J | K | L |
|---|---|---|---|---|---|---|
| HOURS ON STREAM | 166.33 | 190.83 | 222.88 | 251.22 | 262.50 | 269.92 |
| TEMPERATURE °C. | 265.00 | 222.00 | 219.00 | 219.50 | 262.00 | 219.00 |
| PRESSURE PSIG | 230.00 | 230.00 | 235.00 | 240.00 | 240.00 | 240.00 |
| SV NL/GFE/HR | 0.63 | 0.29 | 0.28 | 0.53 | 0.53 | 1.19 |
| FEED [$H_2/CO$] | 1.92 | 1.92 | 0.63 | 0.63 | 0.63 | 1.92 |
| SYNGAS CONV % | 57.81 | 46.12 | 48.61 | 25.24 | 84.52 | 12.74 |
| $H_2$ CONV % | 39.70 | 28.63 | 45.94 | 25.17 | 79.69 | 9.03 |
| CO CONV % | 92.64 | 79.77 | 50.29 | 25.28 | 87.57 | 19.87 |
| HYDROCARBON SELECTIVITIES, WT % OF HC | | | | | | |
| $CH_4$ | 11.69 | 6.49 | 2.22 | 2.13 | 4.39 | 4.10 |
| $C_2H_6$ | 3.40 | 1.80 | 0.49 | 0.61 | 1.28 | 0.00 |
| $C_2H_4$ | 3.32 | 2.17 | 1.33 | 1.18 | 2.21 | 3.12 |
| $C_3H_8$ | 2.35 | 1.70 | 0.66 | 0.62 | 0.88 | 1.22 |
| $C_3H_6$ | 5.91 | 3.36 | 1.92 | 1.81 | 3.87 | 2.77 |
| $C_4H_{10}$ | 1.90 | 1.68 | 0.76 | 0.69 | 0.82 | 1.31 |
| $C_4H_8$ | 4.53 | 2.70 | 1.63 | 1.47 | 2.98 | 1.73 |
| $C_5+$ | 66.91 | 80.10 | 90.98 | 91.50 | 83.56 | 85.75 |
| EXIT [$H_2/CO$] | 15.77 | 6.79 | 0.69 | 0.63 | 1.03 | 2.18 |
| [$H_2 + CO_2/H_2O + CO$] | 41.69 | 42.34 | 8.54 | 5.22 | 26.14 | 5.39 |

EXAMPLE 3

This example illustrates effective selectivation with a wet syngas mixture.

A portion of the catalyst of Example 1A was ground and activated as in Example 1B and put on stream under synthesis conditions for about 7 hours. From about 7 hours to about 22 hours, 0.44 grams of water per gram of catalyst per hour was fed along with 1.23 NL/GFe/hr of dry syngas having a $H_2/CO$ ratio of 1.9, while maintaining the temperature at 260° C and the pressure at 230 psig. The mole fraction of water vapor in the feed represented by the mole ratio:

$$MF_{H_2O} = \frac{H_2O}{H_2 + CO + H_2O}$$

was 0.31 and the mole fraction of hydrogen gas in the feed, computed on a dry basis, represented by $$MF_{H_2} = \frac{H_2}{H_2 + CO}$$

was 0.66.

Figure 3A:
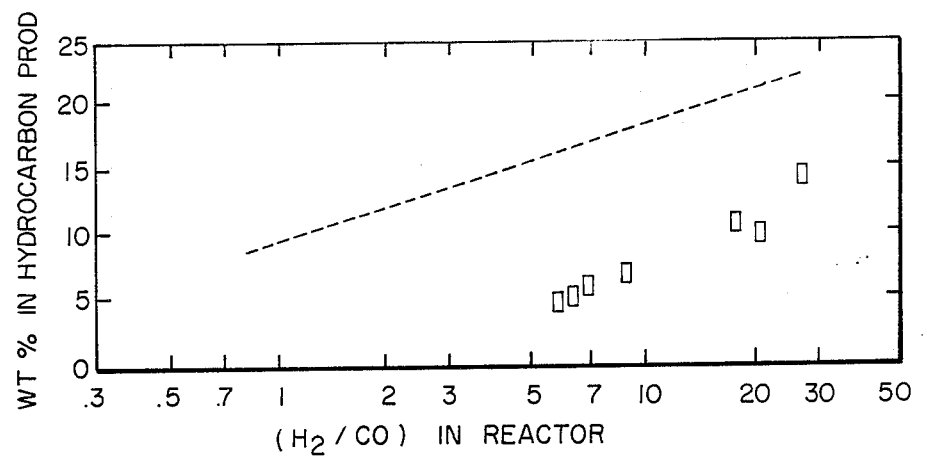
FIGS. 3A and 3B respectively show methane and liquid hydrocarbon ($C_5+$) selectivity as a function of feed composition for Example 3.
Figure 3B:
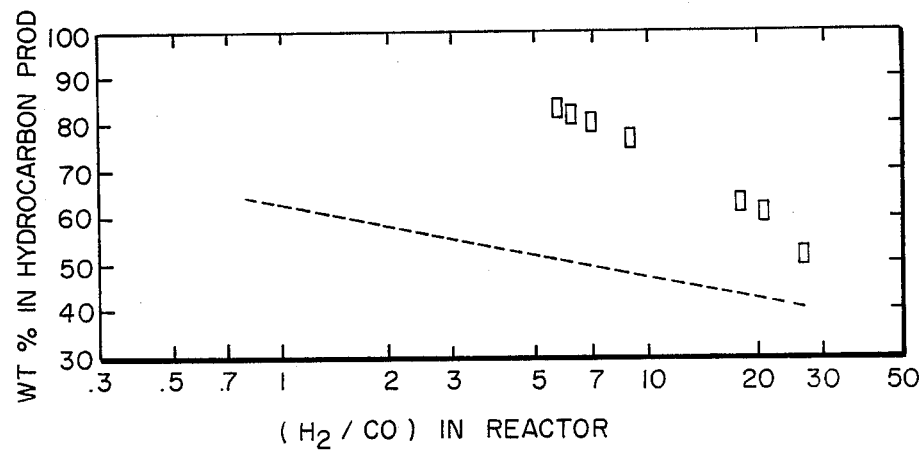

After 22 hours, normal synthesis with substantially dry feed was resumed. The results in Table III show a marked increase in selectivity. FIGS. 3A and 3B respectively show graphically shows the improved performance compared with conventional operation, the latter being represented by the broken line.

TABLE III

| | (EXAMPLE 3) | | | | | | | |
|---|---|---|---|---|---|---|---|---|
| RUN BALANCE | A | B | C | D | E | F | G | H |
| HOURS ON STREAM | 47.25 | 51.33 | 52.92 | 76.55 | 118.78 | 123.58 | 141.33 | 146.33 |
| TEMPERATURE °C. | 265.00 | 265.00 | 266.00 | 265.00 | 265.00 | 264.00 | 264.00 | 266.00 |
| PRESSURE PSIG | 230.00 | 230.00 | 230.00 | 240.00 | 240.00 | 240.00 | 240.00 | 240.00 |
| SV NL/GFE/HR | 1.21 | 2.40 | 3.56 | 0.59 | 0.59 | 2.42 | 0.31 | 2.40 |
| FEED [$H_2/CO$] | 1.86 | 1.86 | 1.86 | 1.86 | 1.86 | 1.86 | 1.86 | 1.86 |
| SYNGAS CONV % | 53.96 | 52.05 | 48.10 | 64.41 | 62.89 | 50.30 | 68.37 | 49.67 |
| $H_2$ CONV % | 36.27 | 35.45 | 32.06 | 47.78 | 46.04 | 33.95 | 53.13 | 33.20 |
| CO CONV % | 86.81 | 82.89 | 77.89 | 95.29 | 94.18 | 80.65 | 96.67 | 80.26 |
| HYDROCARBON SELECTIVITIES, WT % OF HC | | | | | | | | |
| $CH_4$ | 6.87 | 5.49 | 4.70 | 10.16 | 10.39 | 4.92 | 14.19 | 5.04 |
| $C_2H_6$ | 2.01 | 1.33 | 1.04 | 4.67 | 4.96 | 1.12 | 7.35 | 1.11 |
| $C_2H_4$ | 3.20 | 3.14 | 2.95 | 3.22 | 2.85 | 2.86 | 3.17 | 2.85 |
| $C_3H_8$ | 1.30 | 1.17 | 1.11 | 2.51 | 2.64 | 1.14 | 3.85 | 1.15 |
| $C_3H_6$ | 5.36 | 4.71 | 4.33 | 9.28 | 8.64 | 4.12 | 10.87 | 4.14 |
| $C_4H_{10}$ | 1.08 | 0.99 | 0.97 | 2.02 | 2.09 | 1.02 | 2.42 | 1.07 |
| $C_4H_8$ | 3.64 | 3.25 | 3.06 | 7.01 | 5.29 | 3.16 | 5.93 | 3.27 |
| $C_5+$ | 76.52 | 79.93 | 81.83 | 61.14 | 63.14 | 81.66 | 52.22 | 81.37 |
| EXIT [$H_2/CO$] | 8.97 | 7.01 | 5.71 | 20.60 | 17.20 | 6.34 | 26.16 | 6.29 |
| [$H_2 + CO_2/H_2O + CO$] | 22.78 | 17.72 | 14.09 | 35.84 | 30.04 | 15.08 | 44.39 | 15.53 |

EXAMPLE 4

Another portion of the catalyst of Example 1A was taken and the procedure of Example 3 was repeated, except that selectivation was conducted with a reduced amount of water, and for 17 hours instead of 15 hours. Specifically, in the present example, the amount of water fed provided a feed composition having a mole fraction of water vapor $MF_{H_2O}=0.11$ instead of the $MF_{H_2O}=0.31$ of Example 3.

Figure 4A:
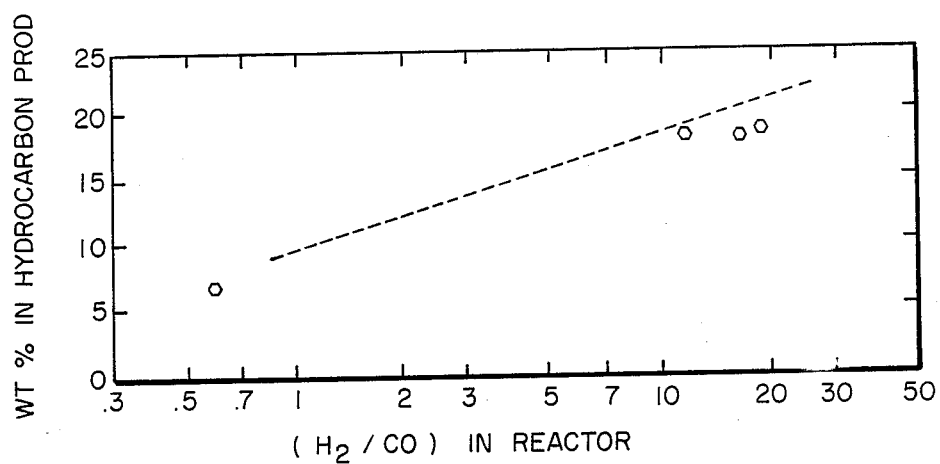
FIGS. 4A and 4B respectively show methane and liquid hydrocarbon ($C_5+$) selectivity as a function of feed composition for Example 4.
Figure 4B:
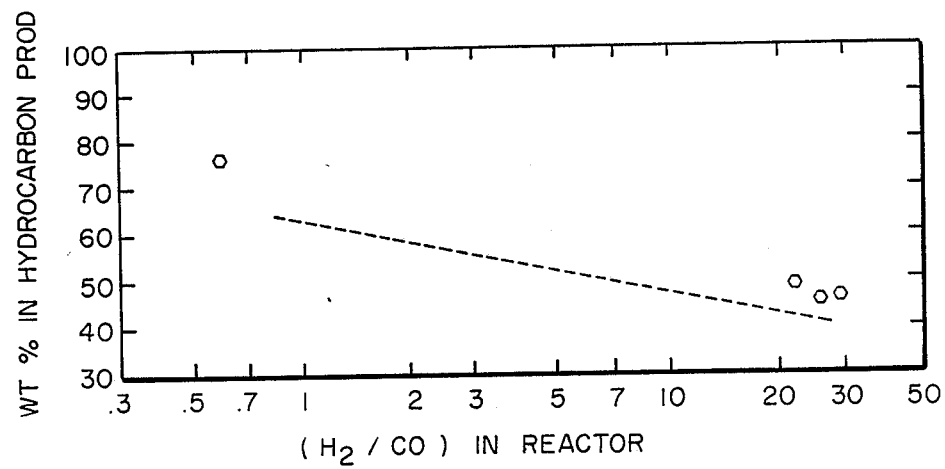

As shown in Table IV and in FIGS. 4A and 4B too low a water vapor pressure in ineffective to provide substantial selectivation.

TABLE IV

| | (EXAMPLE 4) | | | |
|---|---|---|---|---|
| RUN BALANCE | A | B | C | D |
| HOURS ON STREAM | 28.10 | 47.80 | 70.67 | 109.92 |
| TEMPERATURE °C. | 265.00 | 265.00 | 266.00 | 263.00 |
| PRESSURE PSIG | 230.00 | 230.00 | 235.00 | 235.00 |
| SV NL/GFE/HR | 2.41 | 1.26 | 1.26 | 1.23 |
| FEED [$H_2/CO$] | 1.92 | 1.92 | 1.92 | 0.63 |
| SYNGAS CONV % | 55.95 | 62.93 | 62.64 | 84.43 |
| $H_2$ CONV % | 38.21 | 46.46 | 46.42 | 84.99 |
| CO CONV % | 90.08 | 94.60 | 93.84 | 84.08 |
| HYDROCARBON SELECTIVITIES, WT % OF HC | | | | |
| $CH_4$ | 18.02 | 18.46 | 18.06 | 6.44 |
| $C_2H_6$ | 7.28 | 8.23 | 8.07 | 2.94 |
| $C_2H_4$ | 1.25 | 1.26 | 1.34 | 1.16 |
| $C_3H_8$ | 5.12 | 5.85 | 5.62 | 1.48 |
| $C_3H_6$ | 8.92 | 9.49 | 9.71 | 6.10 |
| $C_4H_{10}$ | 3.96 | 4.13 | 4.16 | 1.32 |
| $C_4H_8$ | 6.07 | 6.09 | 6.39 | 4.96 |
| $C_5+$ | 49.38 | 46.50 | 46.66 | 75.99 |
| EXIT [$H_2/CO$] | 11.98 | 19.09 | 16.74 | 0.60 |
| [$H_2 + CO_2/H_2O + CO$] | 43.85 | 45.13 | 42.25 | 19.83 |

EXAMPLE 5-7

Examples 5, 6 and 7 illustrate that the effectiveness of selectivation with a wet synthesis gas feed depends on the carbon monoxide content of the synthesis gas and the mole fraction of water in the feed.

Figure 5A:
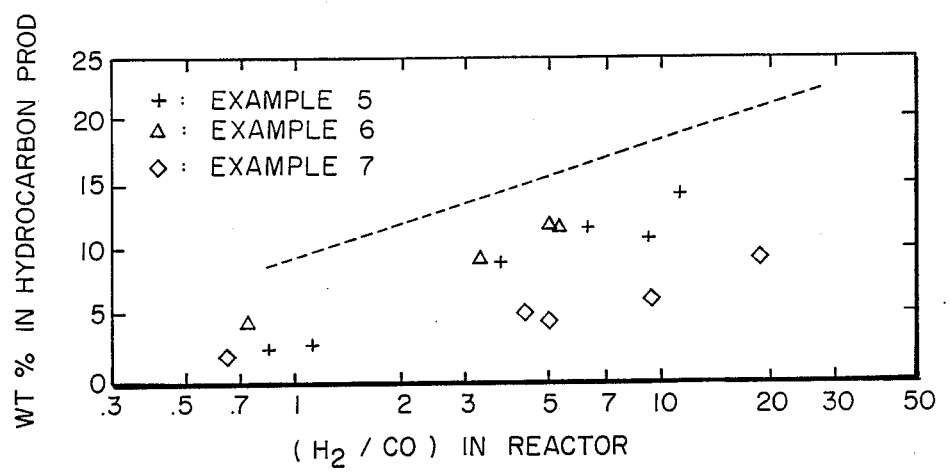
FIGS. 5A and 5B respectively show methane and liquid hydrocarbon ($C_5+$) selectivity as a function of feed composition for Example 5.
Figure 5B:
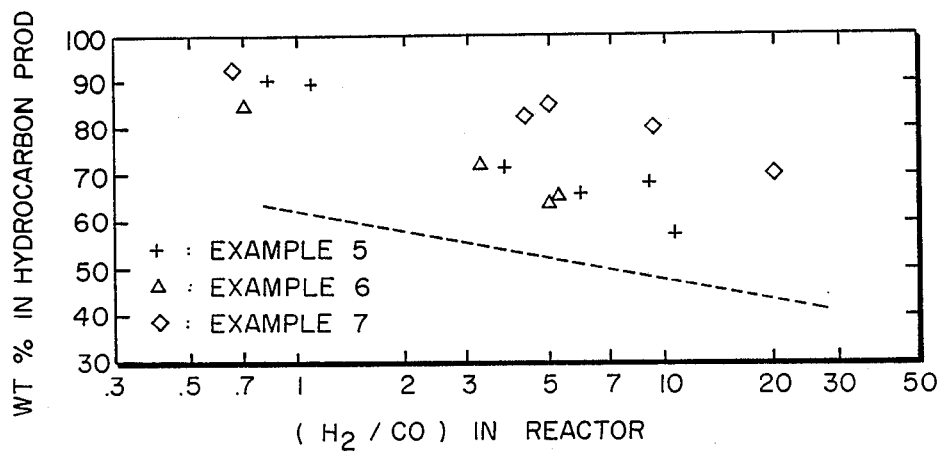

Examples 5, 6 and 7 were conducted with the same sample used in Example 4, in which selectivation had little effect. Examples 5, 6 and 7 show the results of subsequent selectivations, all made with wet syngas having a mole ratio of $H_2/CO$ of 0.64 (instead of 1.9 as in Example 3). In these three examples, the mole fraction of water in the selectivation feed was increased from 0.33 to 0.50 to 0.58 respectively, with evaluation runs with dry syngas made between selectivations. The results are summarized in FIG. 5A. A comparison of FIG. 5A and FIG. 3B shows that although significant selectivation occurs in all of Examples 5, 6 and 7, the selectivation in Example 5 was less than obtained in Example 3, the difference being ascribable to suppression by the higher CO level in the selectivation feed of Example 5. Examples 6 and 7 show that suppression of selectivation by CO can be fully overcome by using an adequately high mole fraction of water.

It will be recognized by one skilled in the art that cofeeding syngas and $CO_2$ will form steam according to Equation (II) above, and that $CO_2$ may be effective for selectivation. We have indeed found this to be true, and such method is contemplated as within the scope of this invention as claimed. However, we find that very high pressures of $CO_2$ are required to give an effective selectivation, and this method is distinctly not preferred.

In the present application including the claims, all references to "syngas", "syngas feed", "dry syngas", and the like, and which are concerned with the feed normally used in the Fischer Tropsch synthesis, are intended to refer to a "substantially dry syngas" as conventionally prepared by steam reforming of methane or by coal gasification, or resulting from conventional recycle operations. "Substantially dry syngas" also may include a carbon-monoxide deficient syngas to which a small amount of steam is added to increase the effective hydrogen to CO ratio to a molar ratio of about 0.7. In all such instances, the "substantially dry syngas" contains a content of $H_2O$ much below that effective for the selectivation step of the present invention.

Cross Reference

The Examiner's attention is called to related copending U.S. Patent Application Serial No. 07/324,796 filed on even date herewith, the entire content of which is incorporated by reference.

What is claimed is:

1. In a conventional medium pressure Fischer Tropach process for synthesis of a hydrocarbon mixture, which process comprises contacting under synthesis conditions a feed consisting of a substantially dry mixture of carbon monoxide and hydrogen carbon with an activated, alkali-promoted precipitated iron catalyst and recovering liquid hydrocarbons, the improvement comprising:

suspending said conventional synthesis;

treating said catalyst for about 0.5 to about 100 hours in a stream consisting essentially of water vapor under a combination of conditions including a temperature of 160 to 400° C., a total pressure of 10 to 1000 psig, and a partial pressure of water vapor effective to selectivate said catalyst; and, resuming said conventional synthesis with said substantially dry mixture of carbon monoxide and hydrogen, whereby increasing the efficiency of said process for synthesizing liquid hydrocarbons.

2. The process described in claim 1 wherein said step of treating is conducted at a temperature of 190° to 350° C. with substantially pure water vapor at a pressure of 15 to 500 psig for about 1 to about 35 hours.

3. The process described in claim 2 wherein about 0.10 to about 1.00 gram of water vapor per gram of Fe per hour is fed to said catalyst.

4. The process described in claim 2 wherein said precipitated iron catalyst has undergone loss of selectivity or loss of activity prior to said step of suspending said synthesis.

5. The process described in claim 1 wherein said step of treating is conducted in a stream of water vapor admixed with carbon dioxide and/or nitrogen gas at a temperature of 190° to 350° C. and a total pressure of 15 to 500 psig for about 1 to about 35 hours, said admixed gas feed containing a mole fraction of water equal to about 0.1 to about 0.75.

6. The process described in claim 5 wherein said precipitated iron catalyst has undergone loss of selectivity or loss of activity prior to said step of suspending said synthesis.

* * * * *

UNITED STATES PATENT AND TRADEMARK OFFICE
CERTIFICATE OF CORRECTION

PATENT NO. : 4,978,689

DATED : 12/18/90

INVENTOR(S) : W.K. Bell et al

It is certified that error appears in the above-identified patent and that said Letters Patent is hereby corrected as shown below:

Col. 13, claim 1, line 31, "carbon" (second occurrence) should be
--gas--

Signed and Sealed this

Sixteenth Day of June, 1992

Attest:

DOUGLAS B. COMER

*Attesting Officer*   *Acting Commissioner of Patents and Trademarks*